(12) United States Patent
Petrich et al.

(10) Patent No.: US 8,119,069 B2
(45) Date of Patent: Feb. 21, 2012

(54) TEST ELEMENT ANALYSIS SYSTEM

(75) Inventors: Wolfgang Petrich, Bad Schonborn (DE); Wilfried Schmid, Mannheim (DE); Gerrit Kocherscheidt, Heddesheim (DE); Jean-Michel Asfour, Weinheim (DE)

(73) Assignee: Roche Diagnostics GmbH, Mannheim (DE)

( * ) Notice: Subject to any disclaimer, the term of this patent is extended or adjusted under 35 U.S.C. 154(b) by 0 days.

(21) Appl. No.: 12/899,921

(22) Filed: Oct. 7, 2010

(65) Prior Publication Data

US 2011/0033341 A1    Feb. 10, 2011

Related U.S. Application Data

(60) Division of application No. 11/769,438, filed on Jun. 27, 2007, which is a continuation of application No. 10/168,959, filed as application No. PCT/DE00/04394 on Dec. 8, 2000, now Pat. No. 7,262,061.

(30) Foreign Application Priority Data

Dec. 24, 1999  (EP) .................................... 99125874

(51) Int. Cl.
G01N 21/00      (2006.01)
(52) U.S. Cl. .................. 422/82.05; 422/82.11
(58) Field of Classification Search ............ 422/82.05, 422/82.11
See application file for complete search history.

(56) References Cited

U.S. PATENT DOCUMENTS

| 4,315,226 A | 2/1982 | Chinone |
| 4,775,637 A | 10/1988 | Sutherland et al. |
| 4,846,548 A | 7/1989 | Klainer |
| 4,849,340 A * | 7/1989 | Oberhardt ................ 435/13 |
| RE33,064 E | 9/1989 | Carter et al. |
| 4,889,401 A | 12/1989 | Klement et al. |
| 4,978,503 A | 12/1990 | Shanks et al. |
| 4,980,278 A | 12/1990 | Yamada et al. |
| 5,071,248 A | 12/1991 | Tiefenthaler et al. |
| 5,127,077 A | 6/1992 | Iyer et al. |
| 5,234,835 A | 8/1993 | Nestor et al. |
| 5,316,727 A | 5/1994 | Suzuki et al. |

(Continued)

FOREIGN PATENT DOCUMENTS

DE     4128846 A1    3/1993

(Continued)

OTHER PUBLICATIONS

Otto S. Wolfbeis, Capillary waveguide sensors, 1996, Elsevier Science, vol. 15, No. 6, p. 225-231.

*Primary Examiner* — Lore Jarrett
(74) *Attorney, Agent, or Firm* — Woodard Emhardt Moriarty McNett & Henry LLP

(57) ABSTRACT

A test element analysis system for the analytical investigation of a liquid sample, comprising a test element including a carrier film having at least one flat side and a test field secured to the flat side and an evaluation instrument including a test element holder for positioning a test element in a measuring position, a measuring device for measuring the optically measurable change in the detection zone, and a housing within the measuring device is positioned. The test element is positioned in the measuring position in such a manner that a first partial section of the test element is located inside the housing and a second partial section is located outside of the housing to be easily accessible.

11 Claims, 3 Drawing Sheets

U.S. PATENT DOCUMENTS

| | | |
|---|---|---|
| 5,397,538 A | 3/1995 | Stark et al. |
| 5,452,716 A | 9/1995 | Clift |
| 5,631,170 A | 5/1997 | Attridge |
| 5,721,102 A | 2/1998 | Vo-Dinh |
| 5,779,978 A | 7/1998 | Hartmann et al. |
| 6,605,804 B1 | 8/2003 | Muller-Fiedler et al. |
| 7,262,061 B2 | 8/2007 | Petrich et al. |

FOREIGN PATENT DOCUMENTS

| | | |
|---|---|---|
| DE | 19828343 A1 | 9/1999 |
| EP | 0047094 A1 | 3/1982 |
| EP | 0234928 A2 | 9/1987 |
| EP | 0 170 376 B1 | 3/1989 |
| EP | 0312293 A2 | 4/1989 |
| EP | 0 171 148 B1 | 4/1991 |
| EP | 0 422 708 B1 | 4/1991 |
| EP | 0585744 A1 | 3/1994 |
| EP | 0 793 090 B1 | 9/1997 |
| GB | 1054767 | 1/1967 |
| WO | WO 88/07666 | 10/1988 |
| WO | WO 99/45369 | 9/1999 |

* cited by examiner

TEST ELEMENT ANALYSIS SYSTEM

CROSS-REFERENCE TO RELATED APPLICATIONS

This application is a divisional application of Ser. No. 11/769,438 filed on Jun. 27, 2007, which is a continuation application of Ser. No. 10/168,959 filed on Mar. 11, 2003, which is now U.S. Pat. No. 7,262,061, issued Aug. 28, 2007, and which is a National Stage of International Application PCT/DE00/04394 filed Dec. 8, 2000, which claims foreign priority benefits of European Application No. 99125874.0 filed Dec. 24, 1999, all of which are hereby incorporated by reference in their entirety.

TECHNICAL FIELD OF THE INVENTION

The invention relates to a test element analysis system for the analytical investigation of a sample, the system comprising test elements and an evaluation instrument.

BACKGROUND OF THE INVENTION

Photometric, carrier-bound tests are used on a large scale to analyze the components in a liquid sample qualitatively and quantitatively, particularly in body fluids of humans or animals. This implies use of test elements which generally contain a reagent system comprising various reagents. To perform a reaction the test element is brought into contact with the sample. The reaction of sample and reagents leads to a change of the test element which is characteristic for the analysis and can be measured optically.

In the medical field, blood and urine are the most important samples. Hereafter, reference is made to blood analysis as an example and without limitation of the general applicability. A particularly important field of application, for which the invention is most suitable, is the control of the blood glucose level of diabetics, in particular the self-monitoring of blood glucose ("home monitoring"). The evaluation instrument provided for measuring the change of the test element which is characteristic for the analysis, and thus for the evaluation of the result of the analysis, is generally adapted to a specific type of test elements of a certain manufacturer. Therefore, the test elements and the evaluation instrument are components which are mutually adapted to each other. As a whole, they are generally designated as analysis system.

The test elements used for photometrical tests have, in most cases, the shape of the known test strips, with at least one test field fixed to a flat side of a generally elongated carrier film made of plastic. In many cases, the test field consists of a plurality of test layers, arranged one on top of the other and containing different components of the reagent system and/or fulfilling different functions. The sample is applied to the upper side of the test field. After the necessary reaction time elapsed, a color change which is characteristic for the analysis can be measured in the detection zone of the test field with the evaluation instrument by reflection-photometrical means. In many cases, the detection zone is located on the bottom side of the test field directed towards the carrier film, and the carrier film comprises a hole in the test field zone, through which the photometrical measurement is performed. The photometrical measurement equipment of the analysis instrument essentially consists of a light emitter (e.g. a light-emitting diode) directed to the detection zone, and a detector, also directed to the detection zone. An analysis system of this type is described, for example, in U.S. Pat. Nos. 5,281,395 and 5,424,035.

Photometrical test element analysis systems allow analyses with high accuracy at low cost, because the test elements can be produced rationally and inexpensively with excellent quality, and because the photometrical measuring technique allows a very exact evaluation of the color development in the detection zone. The handling during measurement is, however, not optimal. In particular, there is a high risk of contamination of the measuring device. This is due to the fact that the test field is—in view of the measuring arrangement necessary for the photometrical measurement—located directly above the illuminating and measuring optical system. To avoid contamination, the sample, e.g. a drop of blood, must be applied very accurately to the test field. This is however not always possible, in particular because diabetics are a very important group of test element analysis system users, and in many cases these patients have, due to their advanced age and their restricted eyesight, difficulties in bringing a blood drop, generated by a puncture in their finger, onto the test field accurately and without contamination of the surrounding areas. Such contamination can lead to a dirt accumulation on the optical measuring system which drastically reduces the accuracy of subsequent measurements. Furthermore, the cleaning of contaminated device parts is unpleasant. In some application cases, such contamination may even cause a danger of infection.

On this basis, the invention addresses the problem of providing a photometrical test element analysis system which allows a high measurement accuracy and simultaneously an easy handling.

SUMMARY OF THE INVENTION

In a photometrical test element analysis system for the analytical investigation of a sample, in particular of a body liquid of human beings or animals, comprising test elements with a carrier film and a test field fixed to a flat side of the carrier film, which test field is, for performing an analysis, brought into contact with the sample in such a way that liquid components of the sample penetrate the test field, the test field containing a reagent system, the reaction of which with the sample leads to an optically measurable change in a detection zone on the side of the test field which faces the carrier film which change is characteristic for the analysis, and an evaluation instrument with a test element holder for positioning a test element in a measuring position and a measuring device for measuring the optically measurable change in the detection zone, the measuring device comprising a light emitter for irradiating primary light onto the detection zone and a detector for the detection of the secondary light diffusely reflected from the detection zone, this problem is solved by the fact that the carrier film of the test element comprises a light guide layer which on its flat side to which the test field is fixed comprises a coupling out zone, in which the detection zone of the test field is in optical contact to the carrier film, this optical contact enabling the coupling out of light from the light guide layer into the detection zone, the primary light of the light emitter is coupled into the light guide layer via an entry surface in such a manner that a light guide section of the light path of the primary light runs between the entry surface and the detection zone in the interior of the light guide layer, the secondary light is reflected from the detection zone into the light guide layer, and a light guide section of the light path of the secondary light runs between the detection zone and the detector in the interior of the carrier film.

The invention also refers to a test element appropriate for such a test element analysis system, as well as a method for performing analyses using the analysis system according to the invention.

The light guide layer consists of a material which is as transparent as possible in the wavelength range of the primary light, thus having the lowest possible optical absorption. Preferably, its refraction index $n_2$ is higher than the refraction index $n_1$ of the adjacent material (e.g. of air, or of a corresponding coating), so that total reflection takes place in the light guide layer. The light guiding mechanism in the light guide layer may also be based on metallic reflection at the boundary surfaces of the light guide layer.

The entry surface, through which the light is coupled into the light guide layer, is preferably formed by a cut surface at an edge side of the light guide layer. In the preferred case of a test strip with a long, stripe-shaped carrier film, the light is coupled in through one of the end faces of the light guide layer. Preferably the primary light is guided under total reflection conditions from the entry surface to the coupling out zone, the latter being a part of one of the two flat sides of the carrier film.

In order to effect the desired coupling out of the light from the light guide layer into the detection zone of the test field in the coupling out zone, different means can be used which will be explained further below. In particular, by appropriate means, the refraction index adjacent the boundary surface of the light guide layer in the coupling out zone is adapted to be not lower, or only a little lower, than the refraction index of the light guide layer, so that total reflection does not, or only to a very low extent take place here. The coupling out can also be supported by roughening the surface of the light guide layer in the coupling out zone. Furthermore, the coupling out of the light can be effected by an appropriate light guidance of the light in the guide layer, such that at least a large share of the primary light in the coupling out zone is incident onto the boundary surface directed towards the test field with an angle which is larger than the limiting angle $\alpha_c$ of the total reflection ($\sin \alpha_c = n_1/n_2$). This can be achieved, in particular, by making the flat side of the light guide layer, opposite to the coupling out zone, inclined, at least in sections, in such a manner that the primary light is reflected into the detection zone.

The secondary light which is diffusely reflected from the detection zone is reflected into the light guide layer and is transported therein for at least a part of the way to the detector, preferably under total reflection conditions. Basically, it is possible to transport the primary light and the secondary light in a single-layer carrier film, i.e. in the same light guide layer. However, an embodiment is preferred in which the carrier film comprises two light guide layers in order to transport the primary light and the secondary light separately. By appropriate measures, to be explained further below, it can be achieved that the light captured by the detector is essentially free from interfering primary light proportions. Thereby a very good signal/noise-ratio is obtained.

Preferably, the carrier film consists essentially of only one or two light guide layers. It is, however, also possible to make a multi-layer carrier film which comprises additional layers for performing other tasks (e.g. with respect to the mechanic characteristics of the carrier film).

In this context it must be taken into account that the light guide layers have a very small cross section. The carrier film should be as thin as possible in order to save material, weight and packaging volume. This results in a very small thickness of the light guide layer or light guide layers which are a part of the carrier film. Preferably, their overall thickness is less than 3 mm, particularly preferred less than 1 mm. Their width (measured in transverse direction to the light transporting direction) is preferably at most 10 mm, particularly preferred at most 6 mm. Based on experimental results, it can be assumed that the thickness of the light guide layers should be at least 10 µm.

The experimental evaluation of the invention has shown that in spite of apparently unfavorable conditions (small entry and cross sectional surface, small primary light intensity in the detection zone) a high measuring accuracy can be obtained. According to the knowledge of the inventors, this can be attributed to the fact that, in comparison to conventional measurements of diffuse reflection of the detection zone of test elements, an increased share of the detected secondary light is captured as useful signal.

At the same time, the invention allows a significant handling simplification, in particular with respect to the contamination-free application of the sample. This is particularly true for a preferred embodiment in which the test field with the blood application site is in the measuring position of the test element located outside the measuring instrument. This allows a so-called "outside dosing" for photometrical analysis systems. So far, this possibility only existed for electrochemical analysis systems, which, however, are less accurate and more costly than photometrical systems. Furthermore, they do not provide the possibility to check the analysis by a visual observation of the color development in the detection zone, as photometrical systems do.

BRIEF DESCRIPTION OF THE DRAWINGS

The invention will hereafter be explained in detail with by means of an embodiment shown in the figures. The technical features described therein can be used individually or in combination in order to create preferred embodiments of the invention. In the figures

DETAILED DESCRIPTION OF THE PREFERRED EMBODIMENTS

Figure 1:
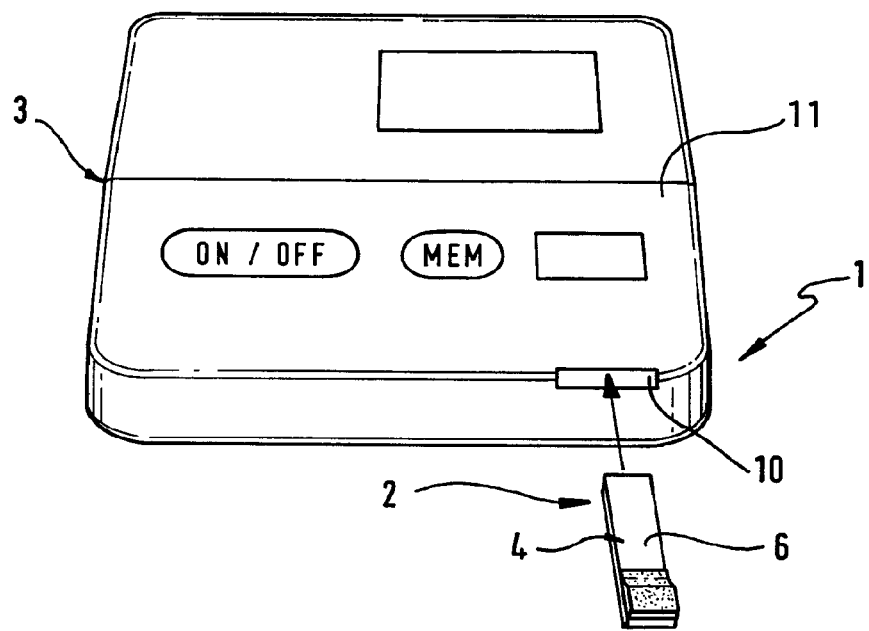
FIG. 1 shows a perspective schematic representation of an analysis system.
Figure 2:
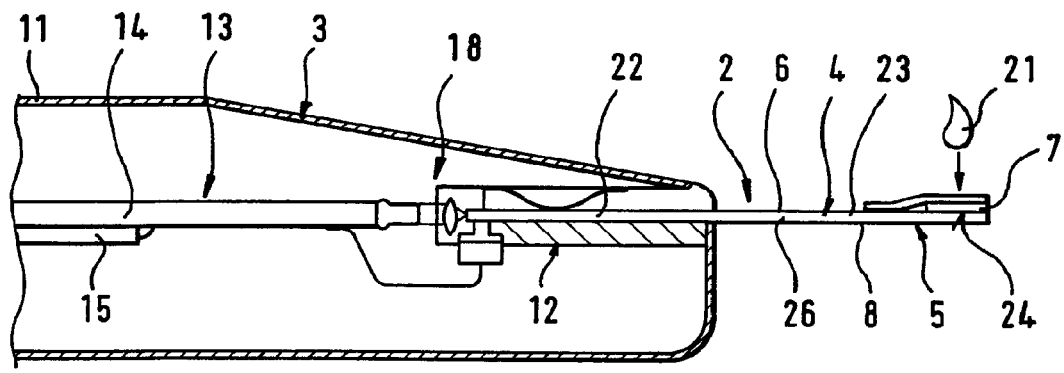
FIG. 2 shows a side view, partially sectional, of an evaluation instrument with a test element in the measuring position.

The analysis system shown in FIGS. 1 and 2 consists of test elements 2 and an evaluation instrument 3. Test element 2 is designed as a test strip 4 with an elongated carrier film 5 made of plastic, carrying a test field 7 which is secured to the upper flat side 6 of the carrier film 5.

Test element 2 is inserted into a test element holder 12 through an aperture 10 in the housing 11 of the evaluation instrument 3, thereby being positioned in the measuring position shown in FIG. 2. The evaluation instrument 3 comprises a measurement and evaluation electronics 13, in the shown case a printed circuit board 14 and integrated circuitry 15. A light emitter 16, preferably a light emitting diode (LED), and a detector 17, preferably a photodiode, both being components of an optical measuring device 18, are connected to the measurement and evaluation electronics 13.

In order to perform an analysis, a drop of sample liquid 21 is applied to the side of the test field 7 opposite to the carrier film 5 (upper side). The sample application is facilitated by the fact that only a first partial segment 22 of the test element 2 is located inside the housing 11 when the test element is positioned in the measuring position, whereas a second partial section 23 carrying the test field 7 protrudes from the housing 11, thus being easily accessible. The liquid penetrates into the test field 7, dissolving the reagents contained in the test field 7, until it reaches the detection zone 24, located at the side of the test field 7 directed towards the carrier film 5 (lower side).

The reaction of the analyte contained in the sample with the reagent system leads to an optically measurable change, in particular a color change, of the detection zone 24. For photometrical evaluation the detection zone 24 is illuminated with primary light and the diffusely reflected secondary light intensity is measured. According to the invention this is achieved by a special design of the test element 2 and of the parts of the optical measuring system 18 cooperating therewith. A preferred embodiment is more clearly shown in FIGS. 3 and 4.

The carrier film 5 includes at least one light guide layer 26 with the explained characteristics with respect to optical transparency and refraction index. Further information on light guide elements, the light transport of which is based on total reflection, can be taken from the relevant literature. In analytical applications, light guides are particularly used in cases where a measurement is to be performed at a place with difficult access (for example, in the interior of a tube or in a vessel inside the human body).

For example, EP 0047094 shows such a measuring probe for measuring different optical characteristics of matter "in situ". U.S. Pat. No. 5,452,716 and Re 33,064 are examples for a type of analytical sensors for analysis based on the attenuated total reflection (ATR) which is observed within a light guide. The interaction between the light guide and the surrounding sample is based on the evanescent field which surrounds a light guide in which total reflection occurs. In another type of fiber-optic sensors discussed in numerous publications a reagent is applied at the end of a light guide fiber, measuring light is guided within the light guide fiber to this end, and the light is changed due to the reaction of the analyte with the reagent (U.S. Pat. Nos. 5,127,077, 5,234, 835). Alternatively a reagent is integrated into the light guide fiber itself (U.S. Pat. No. 4,846,548). In DE 19828343 A1, an optical sensor for the analysis of gases is described, having at least one transparent gas-sensitive layer which is fixed in different positions to a light guide in such a manner that this layer is passed by the light transported through the light guide, in order to measure the absorption or the refraction index in the gas-sensitive layer. Although these previously known methods relate to other fields of application, and differ fundamentally from the present invention, the knowledge about light guide technology from the state of the art, for example concerning appropriate light guide materials, coatings improving the total reflection, etc., can be useful here.

Figure 3:
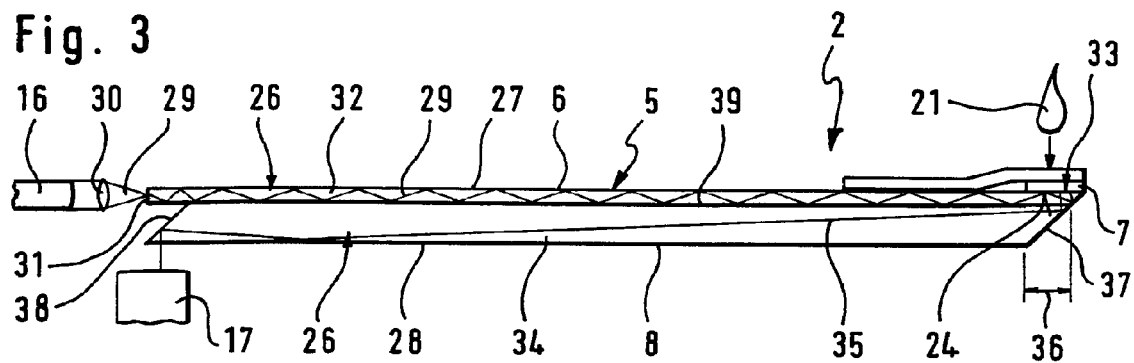
FIG. 3 shows a schematic representation in side view showing the measuring light path in an analysis system according to the invention.
Figure 4:
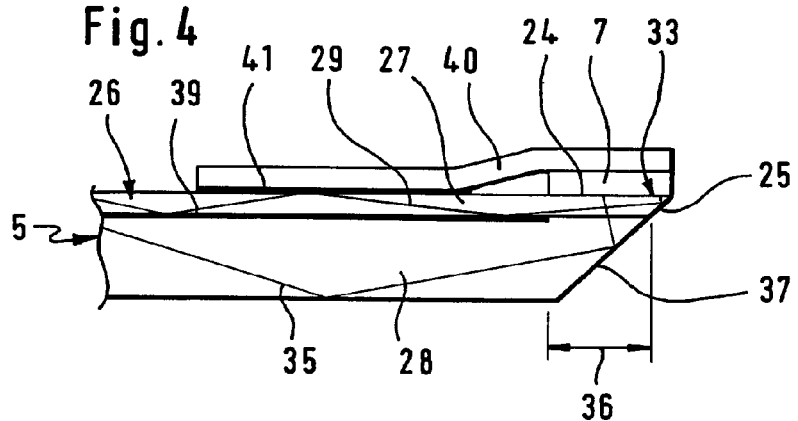
FIG. 4 shows a detail of a partial view of FIG. 3.

The carrier film of the invention comprises preferably, as shown in the FIGS. 3 and 4, two light guide layers 26, the upper light guide layer serving as primary light guide and the lower light guide layer serving as secondary light guide. The primary light 29 is coupled by the light emitter 16 and a lens 30 into the primary light guide 27 through its rear face serving as entrance surface 31 for the coupling in, and is transported inside the primary light guide 27 to the test field 7. The part of the light path of the primary light 29 which is inside the light guide layer 26, is designated light guide section 32. The zone of the upper flat side 6 of the light guide layer 26, which is in line with the test field, serves, at least partially, as coupling out zone 33, where the primary light 29 is coupled out of the light guide layer 27 into the detection zone 24 of the test field 7.

In the embodiment shown, the coupling out of the primary light is essentially effected by the fact that the flat side 8 of the carrier film 5 (for the two-layer embodiment of the carrier film shown, the lower flat side of the primary light guide 27) which is opposed to the coupling out zone 33 (thus, also opposed to the test field 7), is designed in such a manner that the primary light is redirected towards the detection zone 24 of the test field 7. This change of the light propagation direction is effected by a reflecting surface 25, which is inclined at an angle of preferably about 45°. In order to improve its reflecting characteristics, it should be polished and/or equipped with a metallically reflecting coating. Deviations from the angle of 45° are possible, angles between 30° and 60° being preferred.

As an alternative, or additionally, further measures can be taken in order to improve the coupling out of the primary light 29 in the coupling out zone 33. In particular, the test field 7 should be fixed—for example using an index adapted adhesive—in such a manner that in the coupling out zone 33 the refraction index adjacent the surface of the carrier film 5 is not lower, or only insignificantly lower, than the refraction index of the light guide layer 26 itself. In any case, it should be higher than in the section before the light coupling out zone 33.

To the same end, it is also advantageous if the test field is fixed in such a manner and is sufficiently absorbent that liquid sample components are transported in the coupling out zone 33 transported to the flat side 6 of the carrier film, so that the film is wetted in the coupling out zone 33. The refraction index of an aqueous sample liquid is approximately $n=1.33$. This value is significantly lower than the refraction index of the plastic material used for the production of the carrier film 5, which is between 1.4 and 1.7. Nevertheless, the coupling out of primary light 29 is improved by the wetting of the coupling out zone 33 with the sample liquid, because the refraction index of water is significantly higher than the refraction index of air ($n=1$). Finally, the coupling out in the coupling out zone 33 is improved if the surface of the carrier film 5 is roughened.

In order to achieve a very high measuring accuracy, it is advantageous if the test field contains at least in the detection zone components which cause strong optical scattering. Preferably, the scattering coefficient $\mu_s$ is higher than the absorption coefficient $\mu_a$ of the test field material. Particularly preferred, $\mu_s$ is a multiple of $\mu_a$. For example, $\mu_s$ can be 10 times as high, or even 100 times as high as $\mu_a$. The diffuse reflection of the test field material should (before the color development caused by the chemical reaction) be at least about 50%.

The light which as a result of the illumination with the primary light 29 is diffusely reflected from the detection zone 24, falls back as secondary light 35 into the carrier film 5 designed as light guide layer 26. In the shown two-layer embodiment a secondary light guide 28, to a large extent optically separated from the primary light guide 27, is provided for the transport of the light inside the carrier film 5 to the detector 17. In order to improve the selective coupling in of the secondary light 35, it is advantageous if the section 36 of the secondary light guide 28 which is in line with the detection zone 24 is, as shown, at least in sections inclined on the side opposed to the primary light guide 27, in such a manner that the light reflected from the detection zone 24 is reflected by a reflecting surface to the direction of the secondary light guide 28 which leads towards the detector 17. The reflecting surface 37 is parallel to the reflecting surface 25. Preferably, the inclination angles of the reflecting surfaces 25 and 37 to the longitudinal axis of the carrier film 5 is in the vicinity of 45° (approximately between 30° and)60°.

Even if the carrier film 5 contains only one light guide layer 26, it is advantageous if the section of the light guide layer 26 which is aligned with the detection zone 24 is designed, on the side opposed to the test field 7, at least in sections (in particular by at least one reflecting surface inclined with respect to the longitudinal axis of the carrier film 5), in such a manner that the light propagation direction of the irradiated primary light is changed into the direction towards the detection zone, and/or that the light propagation direction of the secondary light diffusely reflected from the detection surface is directed towards the direction of the light guide layer leading to the detector.

The secondary light reflected from the detection zone 24 into the carrier film 5 is transported, on a light guide section 34 of its light path inside the secondary light guide 28, in direction towards the detector 17. In the embodiment shown in FIG. 3, the detector is positioned below the secondary light guide 28 (i.e. on the side opposed to the primary light guide 27). In order to couple the secondary light 35 out from the secondary light guide 38 in direction towards the detector 17, another (polished and/or metalized) reflecting surface, inclined with respect to the longitudinal axis of the carrier film, is provided at the rear end of the carrier film 5 (the end opposed to the test field 7). The angle of inclination of this surface is also preferably in the vicinity of 45° (approximately between 30° and)60° with respect to the longitudinal axis of the carrier film 5.

Instead of the reflecting surfaces 25, 37 and 38, other means can also be used in order to achieve the desired change of the light propagation direction. In particular, this can be obtained by variations of the refraction index at the flat side of the respective light guide layer. Such refraction index variations can be generated, for example, by irradiation with UV laser light.

With respect to an optimum measuring accuracy, it is advantageous to separate the primary light guide 27 optically, as completely as possible, from the secondary light guide 28. For this purpose in the shown preferred embodiment a light barrier 39 is provided between the light guide layers 27 and 28, except for the section 36 which is aligned with the detection zone 24 of the test field 7. The light barrier may comprise one or a plurality of layers.

Preferably, the light barrier 39 includes a barrier layer having a refraction index which is lower than the refraction index of the light guide layers 27, 28. An even better optical separation is obtained if it includes a barrier layer made of a metallically reflecting material.

Figure 5:
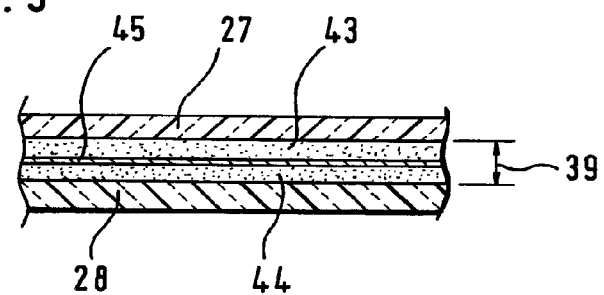
FIG. 5 shows a sectional view of a preferred embodiment of a carrier film.

A particularly preferred three-layer embodiment of the optical barrier is shown in FIG. 5. It consists of three partial layers, namely a first partial layer 43 neighboring to the primary light guide 27, a second partial layer 44 neighboring to the secondary light guide 27, and a metallically reflecting third partial layer inbetween the partial layers 43 and 44. The refraction index of the material from which the partial layers 43 and 44 are made is lower than the refraction index of the neighboring light guide layers 27 and 28, respectively. Preferably, these consist of an adhesive with a corresponding refraction index. The embodiment of the optical barrier shown in FIG. 5 allows, on one hand, a largely loss-free optical guidance in the primary light guide 27 and in the secondary light guide 28, and, on the other hand, a practically complete optical separation.

As mentioned before, the optical barrier 39 does not exist in the section 36 aligned with the detection zone 24. According to a further variant, it can be advantageous if in this zone there is no separation between the layers 27 and 28. In particular, the carrier film 5 can be cut in two layers in longitudinal direction up to the left border (in FIG. 4) of the zone 36, forming the separated light guide layers 27 and 28, whereas in zone 36 it is a one-piece element over its entire thickness.

In the scope of the invention, the test field 7 can be embodied in different ways. In particular, many one-layer or multi-layer analysis element test field embodiments, known according to the state of the art, can be used. It is however essential that an optically measurable change, characteristic for the analysis, takes place in the detection zone 24 on the side of the test field 7 directed towards the carrier film 5.

Further design features of known analytical test elements can also be used in the invention. For example, the test strip 4 shown in FIGS. 2 to 4 is provided with a so-called spreading layer above the test field 7, which itself can have a plurality of layers and may serve for sample preparation purposes. In particular, it may serve for even wetting of the upper side of the test field 7 with the sample liquid 21, or in order to separate the red blood cells from the whole blood or to withdraw excessive amounts of sample liquid. If such a spreading layer 40—as in the shown embodiment—extends beyond the surface area of the test field 7 and is also fixed to the carrier film 5, it is advantageous to provide also here an optical barrier 41 of a material with a low refraction index and/or metallic reflection, thus eliminating a possible interference with the light guide characteristics of the carrier film 5.

The evaluation of the measured signal, i.e. of the measured intensity of the secondary light and the determination of the desired analytical result, for example of the glucose concentration in the sample, is performed by the measurement and evaluation electronics 13, in principle in the same way as in common test element analysis systems, and therefore does not need further explanation.

Figure 6:
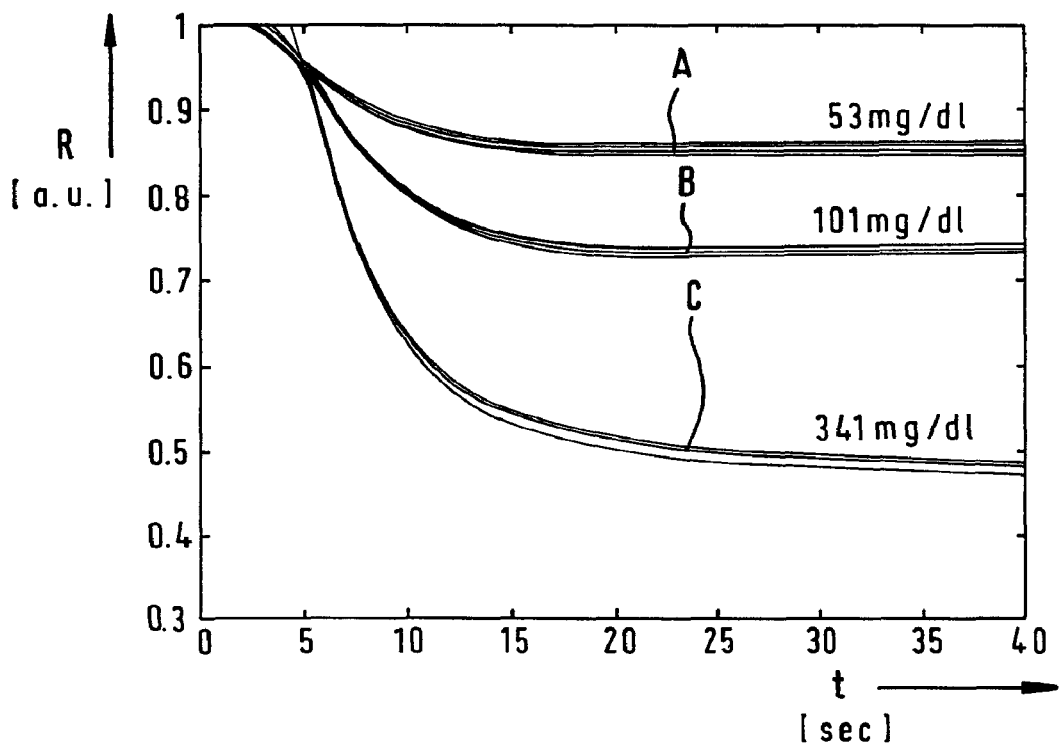
FIG. 6 shows measuring curves of the diffuse reflection of the detection zone versus time for three glucose concentrations.
Figure 7:
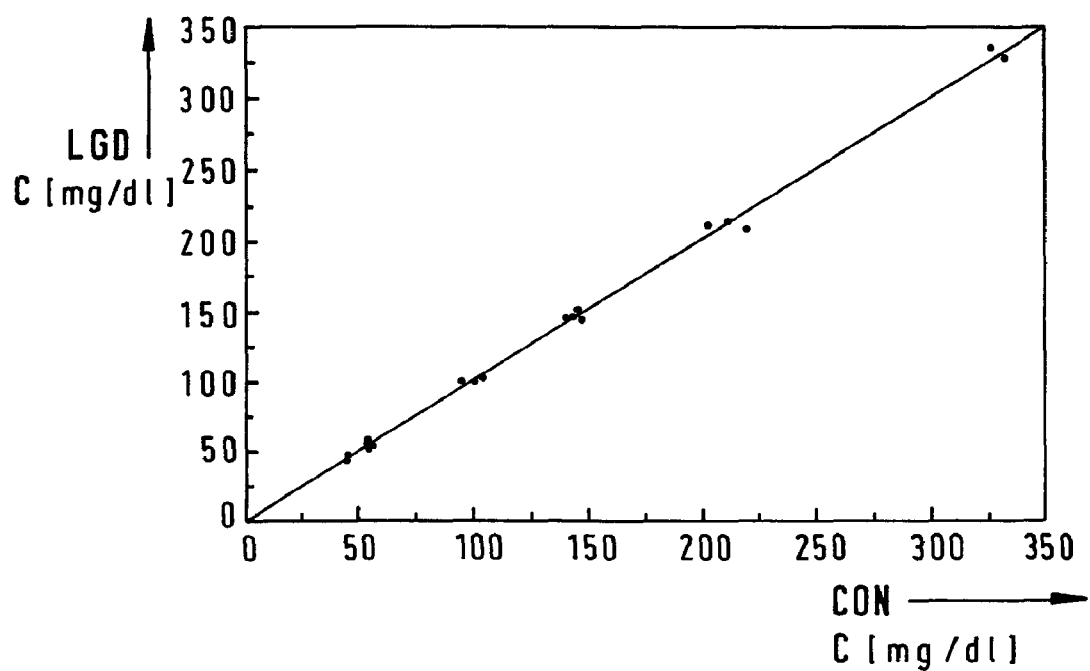
FIG. 7 shows a graphical representation of a comparative measurement with an analysis system according to the invention and with a conventional analysis system.

FIG. 6 shows measurement results obtained with an analysis system the essential design features of which correspond to FIGS. 2 to 4. Here, the intensity of the secondary light is shown in arbitrary units versus the time t in seconds. The structure and the chemical composition of the test field 7 correspond to a commercially available analysis element glucose test. The figure shows measuring curves with a plurality of measurements for each of three different glucose concentrations, namely Curve A: 53 mg/di
Curve B: 101 mg/dl
Curve C: 341 mg/dl It can easily be seen that the measurement signal is very well reproducible for a plurality of measurements, and that the differences of the measurement curves in dependence on the glucose concentration (the signal amplitude) allow an accurate evaluation.

FIG. 6 shows a system comparison wherein measuring values of the glucose concentration C according to the invention-related are plotted on the ordinate marked with LGD, and measuring values measured with a conventional test element analysis system are plotted on the abscissa, marked with CON (for "conventional"). The results show a practically complete match.

What is claimed is:

1. A test element analysis system for the analytical investigation of a liquid sample, comprising:

a test element including a carrier film having at least one flat side and a test field secured to the flat side, the test field configured to be contacted, in order to perform an analysis, with a liquid sample in such a manner that liquid sample components penetrate into the test field, the test field containing a reagent system comprising a soluble reagent and a detection zone located on a side of the test field directed towards the carrier film, a reaction of the reagent system with at least one component of the sample causing an optically measurable change in the detection zone, said optically measurable change being characteristic for the analysis; and an evaluation instrument including a test element holder for positioning the test element in a measuring position, a measuring device for measuring the optically measurable change in the detection zone, and a housing containing the measuring device, the measuring device including a light emitter for irradiating primary light onto the detection zone, and a detector for detecting secondary light diffusely reflected from the detection zone;

the carrier film comprising at least one light guide layer and a coupling out zone, the carrier film having an elongated, strip-shaped form and a longitudinal dimension, the coupling out zone being a part of the flat side of the carrier film to which the test field is fixed and within which the detection zone of the test field is in optical contact with the carrier film in such a manner that light is coupled out from the light guide layer into the detection zone;

the primary light of the light emitter being coupled into the light guide layer via an entry surface, in such a manner that the light guide layer provides a light guide section for the light path of the primary light between the entry surface and the detection zone running inside the interior of the light guide layer along the longitudinal dimension of the carrier film;

secondary light which is diffusely reflected from the detection zone being reflected into the light guide layer and the light guide layer providing a light guide section for the light path of the secondary light running inside the carrier film along the longitudinal dimension of the carrier film between the detection zone and the detector;

the test element being positioned in the measuring position in such a manner that a first partial section of the test element is located inside the housing and a second partial section is located outside of the housing to be easily accessible;

and the entry surface being located in the first partial section, and the test field being located in the second partial section.

2. The test element analysis system according to claim 1 wherein the liquid sample comprises a body liquid of human beings or of animals.

3. The test element analysis system according to claim 1 wherein the carrier film comprises a plastic material.

4. The test element analysis system according to claim 1 wherein the side of the light guide layer opposed to the coupling out zone is adapted, at least in sections thereof, to cause a change of the light propagation direction of the primary light towards the detection zone.

5. The test element analysis system according to claim 1 wherein the side of the light guide layer which is opposed to the detection zone is adapted, at least in sections thereof, to cause a change of the propagation direction of the secondary light diffusely reflected from the detection zone, to coincide with the direction of the light guide layer leading towards the detector.

6. The test element analysis system according to claim 1 wherein the test field is sufficiently absorbent to transport liquid sample components in the coupling out zone to the flat side of the carrier film to which the test field is secured in such a manner that the liquid sample components wet the light guide layer in the coupling out zone.

7. The test element analysis system according to claim 1 wherein the light guide layer in the coupling out zone is roughened in order to improve the coupling out of the primary light.

8. The test element analysis system according to claim 1 wherein the test field contains components causing strong optical diffusion.

9. The test element analysis system according to claim 1 wherein the carrier film comprises two light guide layers, wherein the primary light is coupled into a first light guide layer serving as primary light guide, and the secondary light from the detection zone is coupled into a second light guide layer serving as secondary light guide.

10. The test element analysis system according to claim 9 wherein the test field is fixed to the flat side of the primary light guide and the test field and the secondary light guide are located on opposed sides of the primary light guide.

11. The test element analysis system according to claim 9 wherein the light guide layers are separated, at least on a part of their length, by an optical barrier.

* * * * *